United States Patent
Wang (10) Patent No.: US 8,928,332 B2
(45) Date of Patent: Jan. 6, 2015

(54) ELECTRICAL IMPEDANCE IMAGING

(75) Inventor: Wei Wang, Leicester (GB)

(73) Assignee: WZVI Limited, London (GB)

( * ) Notice: Subject to any disclaimer, the term of this patent is extended or adjusted under 35 U.S.C. 154(b) by 354 days.

(21) Appl. No.: 13/384,072

(22) PCT Filed: Jul. 15, 2010

(86) PCT No.: PCT/GB2010/001355
§ 371 (c)(1),
(2), (4) Date: Mar. 30, 2012

(87) PCT Pub. No.: WO2011/007147
PCT Pub. Date: Jan. 20, 2011

(65) Prior Publication Data
US 2012/0200302 A1    Aug. 9, 2012

(30) Foreign Application Priority Data

Jul. 15, 2009  (GB) .................. 0912316.7

(51) Int. Cl.
*G01R 27/00*   (2006.01)
*A61B 5/053*   (2006.01)

(52) U.S. Cl.
CPC ............ *A61B 5/0536* (2013.01); *A61B 5/0537* (2013.01); *A61B 5/053* (2013.01); *A61B 2562/0209* (2013.01); *A61B 2562/046* (2013.01)
USPC .................. 324/600; 324/86; 324/750.12

(58) Field of Classification Search
USPC ............ 324/600, 602–613, 167, 86, 208.25, 324/631, 76.11, 444–449, 500, 515
See application file for complete search history.

(56) References Cited

U.S. PATENT DOCUMENTS

| 4,539,640 A | 9/1985 | Fry et al. ................. 364/414 |
| 5,291,888 A | 3/1994 | Tucker ..................... 128/644 |
| 6,122,544 A * | 9/2000 | Organ ....................... 600/547 |
| 2004/0210158 A1 | 10/2004 | Organ et al. ............... 600/547 |
| 2004/0243018 A1 | 12/2004 | Organ et al. ............... 600/547 |
| 2008/0108909 A1 | 5/2008 | Reger et al. ............... 600/546 |

FOREIGN PATENT DOCUMENTS

| CA | 2 272 429 A1 | 6/1998 |
| CN | 2902191 Y | 5/2007 |
| WO | WO 98/23204 | 6/1998 |
| WO | WO 02/09584 A1 | 2/2002 |
| WO | WO 2004/043253 A1 | 5/2004 |
| WO | WO 2007/017634 A2 | 2/2007 |
| WO | WO 2007/035887 A2 | 3/2007 |
| WO | WO 2008/075250 A1 | 6/2008 |
| WO | WO 2009/018620 A1 | 2/2009 |

OTHER PUBLICATIONS

"Impedance Tomography": Chapter 26 of Bioelectromagnetis, J Malmivuo and R Plonsey, 1995 (8 pages).

(Continued)

*Primary Examiner* — Melissa Koval
*Assistant Examiner* — Trung Nguyen
(74) *Attorney, Agent, or Firm* — Harrington & Smith (57) ABSTRACT

An apparatus for electrical impedance imaging has electrodes arranged on an electrode carrier in an arrangement including a unit of repetition. The unit of repetition repeats over the electrode carrier and has an angle of rotational symmetry less than 90°. Specifically, the unit of repetition is an equilateral triangle or a hexagon.

20 Claims, 6 Drawing Sheets

(56) References Cited

OTHER PUBLICATIONS

"A comparison of headnet electrode Arrays for electrical impedance tomography of the human head", AT Tidswell, AP Bagshaw, DS Holder, RJ Yerworth, L Eadie, S Murray, L Morgan and RH Bayford, Physiological Measurement, 24, 527, 2003, (19 pages).

"The design of De Montfort MK2 Electrical Impedance Mammography system", W Wang, B Tunstall, D Chauhan and M McCormick, Proceedings of the 20th Annual International Conference of the IEEE Engineering in Medicirg and Biology Society, 20, 1998, (pp. 1042-1043).

"Distinguishability of inhomogeneities using planar electrode arrays and different patterns of applied excitation", T-J Kao, JC Newell, GJ Saulnier and D Isaacson, Physiological Measurement, 24, 2003, (pp. 403-411).

FDA Summary of Safety and Effectiveness Data for T-Scan 2000 (available from http://www.accessdata.fda.gov/cdrh_docs/pdf/P970033b.pdf), (26 pages).

* cited by examiner

ELECTRICAL IMPEDANCE IMAGING

FIELD OF THE DISCLOSURE

The present disclosure relates to an apparatus for electrical impedance imaging and a method of electrical impedance detection. Such an apparatus and method has application in medical diagnostics.

BACKGROUND TO THE DISCLOSURE

Electrical impedance detection, as used in Electrical Impedance Mammography (EIM) and Electrical Impedance Imaging (EII), also referred to as Electrical Impedance Tomography (EIT), Electrical Impedance Scanning (EIS) and Applied Potential Tomography (APT), can provide an image of the spatial distribution of electrical impedance inside body tissue. This is attractive as a medical diagnostic tool because it is non-invasive and does not use ionizing radiation as in X-ray tomography or strong, highly uniform magnetic fields as in Magnetic Resonance Imaging (MRI).

Typically a two dimensional or three dimensional array of evenly spaced electrodes is attached to the body tissue about the region of interest. Voltages are applied across pairs of input electrodes, and output electric currents are measured at output electrodes. Alternatively, input electric currents are applied between pairs of input electrodes, and output voltages are measured at output electrodes or between pairs of output electrodes. For example, a very small alternating electric current is applied between one pair of electrodes, and the voltage between all other pairs of electrodes is measured. The process is then repeated with the electric current applied between a different pair of the electrodes.

The measured values of the voltage depend on the electrical impedance of the body tissue, and from these values an image is constructed of the electrical impedance of the body tissue. By performing a plurality of such measurements, both two dimensional and three dimensional images can be constructed. Spatial variations revealed in electrical impedance images may result from variations in impedance between healthy and non-healthy tissues, variations in impedance between different tissues and organs, or variations in apparent impedance due to anisotropic effects, for example resulting from muscle alignment.

Tissue or cellular changes associated with cancer cause significant localised variations in electrical impedance, and electrical impedance images can be used to detect breast carcinomas or other carcinomas.

The electric current or voltage applied to the electrodes may have a broad range of different frequencies. Different morphologies that have an insignificant impedance at one frequency may have a more significant variation in impedance at a different frequency. Also, different frequencies may penetrate the object to different depths, and reflections which can cause noise in images may vary with the frequency of the applied electric currents or voltages.

SUMMARY OF THE DISCLOSURE

According to a first aspect of the disclosure, there is provided an apparatus for electrical impedance imaging, the apparatus comprising electrodes arranged on an electrode carrier in an arrangement comprising a unit of repetition that repeats over the electrode carrier and that has an angle of rotational symmetry less than 90°.

According to a second aspect of the disclosure, there is provided a method of electrical impedance detection, comprising employing an electrode carrier having electrodes arranged on the electrode carrier in an arrangement comprising a unit of repetition that repeats over the electrode carrier and that has an angle of rotational symmetry less than 90°.

Electrodes deployed in such a manner enable measurement of electrical impedance to be made using a pattern of electrodes rotated through successive positions by a rotational displacement which is less than 90°, without rotating the electrode carrier and the electrodes physically. Therefore, the apparatus enables measurements of electrical impedance to be made with a finer resolution than the use of electrodes arranged in a rectangular grid, which enables rotation of a pattern of electrodes by multiples of 90° without rotating an electrode carrier. In other words, the apparatus enables measurements of electrical impedance to be made with rotational resolution less than 90° by selection of electrodes without rotating the electrode carrier and electrodes physically, in contrast to the use of a rectangular grid of electrodes which would require rotation of an electrode carrier to achieve the same rotational resolution.

In addition, electrodes deployed in such a manner enable measurement of electrical impedance to be made using a pattern of electrodes in different locations on the electrode carrier, where the pattern can be the same in each location. This facilitates comparison of measurements made in different locations of the electrode carrier.

Optionally, the unit of repetition can overlap from one repetition to another. This feature enables electrical impedance imaging with a fine resolution.

Optionally, the arrangement can comprise one or more different units of repetition that each repeat over the electrode carrier and have angles of rotational symmetry less than 90°. This feature enables electrical impedance imaging to be performed using initially a first unit of repetition providing, for example, a relatively coarse resolution for quickly identifying regions of interest in an object, followed by the use of a second unit of repetition providing a finer resolution for more detailed examination of an identified region.

Optionally, the angles of rotational symmetry can be equal. That is, the angle of rotational symmetry and another angle of rotational symmetry can be equal. This feature can reduce the number of electrodes required.

Optionally, the different unit(s) of repetition can have a different number of the electrodes. This feature can enable the speed of electrical impedance imaging to be increased. For example, initially a first unit of repetition using relatively few electrodes may be used for quickly identifying regions of interest in an object, followed by the use of a second unit of repetition with more electrodes providing a finer resolution for more detailed examination of an identified region.

Optionally, the different unit(s)s of repetition can extend across areas of different sizes. This feature can enable the speed of electrical impedance imaging to be increased. For example, initially a first unit of repetition extending across a relatively large area may be used for quickly identifying regions of interest in an object, followed by the use of a second unit of repetition extending over a smaller area for providing a finer resolution for more detailed examination of an identified region.

Optionally, the electrodes can be arranged at one or more corners of each triangle of a tessellation of triangles. In particular, the triangles can be equilateral triangles.

Furthermore, the triangles can be of equal size. Such an arrangement enables a rotational displacement which is a multiple of 60°.

Optionally, the apparatus can comprise:

means for applying a first input electrical signal at a first input electrode pair of the electrodes;

means for detecting first output electrical signals at a first output electrode group of the electrodes;

means for applying a second input electrical signal at a second input electrode pair of the electrodes; and means for detecting second output electrical signals at a second output electrode group of the electrodes;

wherein the second input electrode pair is aligned relative to the first input electrode pair at an angle of rotational displacement equal to a multiple of (one of) the angle(s) of rotational symmetry.

Correspondingly, the method of electrical impedance detection can comprise: applying a first input electrical signal at a first input electrode pair of the electrodes;

detecting first output electrical signals at a first output electrode group of the electrodes;

applying a second input electrical signal at a second input electrode pair of the electrodes; and detecting second output electrical signals at a second output electrode group of the electrodes;

wherein the second input electrode pair is aligned relative to the first input electrode pair at an angle of rotational displacement equal to a multiple of (one of) the angles of rotational symmetry.

In particular, the angle of rotational displacement can be equal to (one of) the angles of rotational symmetry.

An angle of rotational displacement which is a multiple of one of the angles of rotational symmetry for applying the input electrical signals enables electrical impedance measurements to be made having improved resolution. Where the electrodes are arranged at one or more corners of each triangle of a tessellation of equal size equilateral triangles, the rotational resolution can be 60°.

Optionally, the apparatus can comprise means for selecting the angle of rotational displacement from at least two of the set 60°, 120° and 180°. Correspondingly, the method can comprise selecting the angle of rotational displacement from at least two of the set 60°, 120° and 180°.

By selecting the angle of rotational displacement for applying input electrical signals, flexibility in making electrical impedance measurements is provided. For example, a single angle of rotational displacement may be selected, or the angle of rotational displacement may be varied, such as by using a coarse rotational resolution initially for quickly identifying regions of interest in an object, and then by using a finer rotational resolution for a more detailed examination of an identified region. Using a rotational resolution of 60° for applying input electrical signals, a total of six rotational positions are available, namely 0°, 60°, 120°, 180°, 240° and 300°. However, the rotational positions of 240° and 300° may be considered to be a rotational position of 120° and 60° respectively.

Optionally, the apparatus can comprise means for selecting a spacing of the electrodes of the first input electrode pair and a spacing of the electrodes of the second input electrode pair. Correspondingly, the method can optionally comprise selecting the spacing of the electrodes of the first input electrode pair and the spacing of the electrodes of the second input electrode pair. This feature provides flexibility in making electrical impedance measurements. For example, a relatively large spacing enables electrical impedance measurements to be made at a larger depth in an object, whereas a relatively small spacing enables electrical impedance measurements to be made having a high resolution. A larger spacing may be used initially for quickly identifying regions of interest in an object, and then a smaller spacing may be used for more detailed examination of an identified region.

Optionally, the electrodes of the first input electrode pair and of the first output electrode group can constitute a first electrode set having a first pattern, and the electrodes of the second input electrode pair and of the second output electrode group can constitute a second electrode set having a second pattern, and the second pattern can be identical to the first pattern rotated by the angle of rotational displacement. Use of such an identical pattern facilitates comparison of electrical impedance for different rotational displacements and detection of electrical impedance with a high resolution, thereby facilitating detection of characteristics of an object under evaluation.

Optionally, the apparatus can comprise means for selecting a number of electrodes in the first and second electrode sets. Correspondingly, the method can optionally comprise selecting a number of electrodes in the first and second electrode sets. This feature provides flexibility in making electrical impedance measurements. For example, a high number of electrodes may be selected for a large object under evaluation and a low number of electrodes may be selected for a small objection under evaluation. This can facilitate analysis of electrical impedance data by eliminating or reducing redundant data. As another example, a high number of electrodes may be used initially for quickly identifying regions of interest in an object, and then a small number of electrodes may be used for more detailed examination of an identified region.

The first pattern, and the identical second pattern, may be fixed or variable. Therefore, as a further feature, the apparatus can optionally comprise means for selecting the first pattern. Correspondingly, the method can optionally comprise selecting the first pattern. This feature provides flexibility in making electrical impedance measurements. For example, the first pattern may be selected to correspond to the shape of the object under evaluation. This can facilitate analysis of electrical impedance data by eliminating or reducing redundant data. As another example, a large first pattern may be used initially for quickly identifying regions of interest in an object, and then a first pattern matched to the shape of the region of interest may be used for more detailed examination of an identified region.

The first pattern may be devised by an operator or may be fixed. Therefore, as a further feature, the apparatus can optionally comprise means for selecting the first pattern from a plurality of fixed patterns. Correspondingly, the method can optionally comprise selecting the first pattern from a plurality of fixed patterns. This feature facilitates making electrical impedance measurements by removing or reducing the need for a first pattern to be devised for each object under evaluation. Suitable candidate first patterns can be stored in readiness for selection. The candidate first patterns may be, for example, suitable for typical objects to be evaluated.

Optionally, the boundary of the first pattern can be a hexagon, the hexagon having sides of length corresponding to a multiple of the length of a side of the equilateral triangles. A hexagon is a compact pattern that enables the same region of an object to be evaluated using the first electrode set and the second electrode set with the same electrodes.

Optionally, the first input electrode pair can comprise electrodes at opposite corners of the hexagon and the first output electrode group can comprise all other electrodes of the first electrode set. This feature can enable all electrodes of the first output electrode group to be used for detecting the first output electrical signals.

Optionally, the electrodes of the first electrode set can be a subset of the electrodes of the electrode carrier which form the hexagon. This feature can facilitate collection and analysis of electrical impedance data by eliminating or reducing redundant data.

Optionally, the means for detecting the first output electrical signals can be operable to detect the first output electrical signals at a plurality of combinations of electrodes of the first output electrode group, and the means for detecting the second output electrical signals is operable to detect the second output electrical signals at a plurality of combinations of electrodes of the second output electrode group. This feature enables electrical impedance to be detected with high resolution.

Optionally, the apparatus can comprise means for selecting a spacing of the electrodes of each of the combinations of electrodes. Correspondingly, the method can comprise selecting a spacing of the electrodes of each of the combinations of electrodes. This feature provides flexibility in making electrical impedance measurements. For example, a relatively large spacing enables electrical impedance measurements to be made at a larger depth in an object, whereas a relatively small spacing enables electrical impedance measurements to be made having a high resolution. A larger spacing may be used initially for quickly identifying regions of interest in an object, and then a smaller spacing may be used for more detailed examination of an identified region.

Optionally, the plurality of combinations of electrodes of the first output electrode group can be parallel to a line joining the electrodes of the first input electrode pair, and the plurality of combinations of electrodes of the second output electrode group can be parallel to a line joining the electrodes of the second input electrode pair. The use of such combinations can enable the first and second output electrical signals to be detected along lines of greatest voltage gradient, thereby contributing to a high accuracy of electrical impedance detection.

Optionally, the parallel combinations of electrodes can comprise parallel combinations of two adjacent electrodes. This feature can enable the number of parallel combinations to be maximised, thereby contributing to a high accuracy of electrical impedance detection.

Optionally, the apparatus can comprise means for applying a third input electrical signal at a third input electrode pair of the electrodes and means for detecting third output electrical signals at a third output electrode group of the electrodes, wherein the third input electrode pair is displaced from the first input electrode pair and the third output electrode group is displaced from the first output electrode group by a common distance and a common direction. Correspondingly, the method can comprise applying a third input electrical signal at a third input electrode pair of the electrodes and detecting third output electrical signals at a third output electrode group of the electrodes, wherein the third input electrode pair is displaced from the first input electrode pair and the third output electrode group of electrodes is displaced from the first output electrode group by a common distance and a common direction. This feature provides flexibility in making electrical impedance measurements. For example, displacement of electrodes by a common distance and a common direction may be used initially for quickly identifying regions of interest in an object, and then rotational displacement of electrodes may be used for more detailed examination of an identified region.

Optionally, the electrode carrier can be at least part of a base of a receptacle for electrical impedance imaging of an object located within the receptacle, and the receptacle can comprise further electrodes arranged on a wall of the receptacle for electrical impedance imaging of an object located within the receptacle. This feature facilitates two-dimensional electrical impedance imaging with a high sensitivity at greater distances from the electrode carrier by enabling current density to be increased at distances from the electrode carrier.

Optionally, the electrode carrier can be rotatable relative to the wall. Correspondingly, the method can comprise rotating the electrode carrier relative to the wall. This feature enables increased rotational resolution.

Optionally, the apparatus can comprise a spacing member for spacing the object from the electrode carrier. Correspondingly, the method can comprise spacing the object from the electrode carrier. By means of this feature, during rotation of the electrode carrier, the transfer of a rotational force from the rotating carrier to the object under evaluation can be reduced or eliminated, thereby decreasing patient discomfort.

Optionally, the spacing member can be electrically conductive. Optionally, the spacing member can have a conductivity less than the conductivity of the object. These features can reduce electrical influence of the spacing member on electrical impedance detection.

Optionally, the apparatus can comprise an electrically conductive liquid in the receptacle, wherein the spacing member has a conductivity at least 90% of the conductivity of the liquid. Correspondingly, the method can comprise providing an electrically conductive liquid in the receptacle, wherein the spacing member has a conductivity at least 90% of the conductivity of the liquid. This feature can provide improved electrical coupling between the electrode carrier and the object under evaluation. In one embodiment, the conductivity of the spacing member can be substantially equal to the conductivity of the liquid.

Optionally, the liquid can have a conductivity in the range 10 to 12 mS/cm. Such a range of conductivity is suited to typical objects to be evaluated by electrical impedance detection, such as human breast tissue.

BRIEF DESCRIPTION OF THE DRAWINGS

Preferred embodiments will now be described, by way of example only, with reference to the accompanying drawings, in which.

DETAILED DESCRIPTION OF PREFERRED EMBODIMENTS

Figure 1:
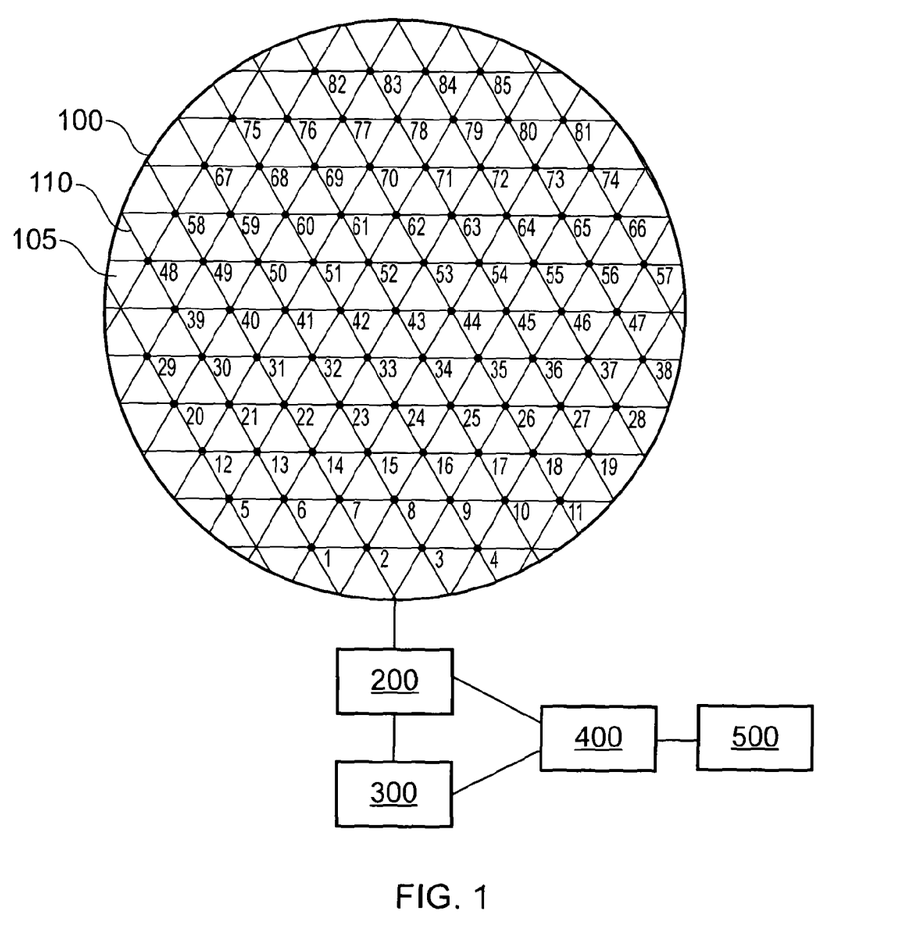
FIG. 1 is schematic diagram of an apparatus for electrical impedance imaging.

Referring to FIG. 1, there is a circular carrier 100 which is electrically non-conductive and which may be made, for example, of a plastic material. Electrodes 1-85 are deployed across a flat surface 105 of the electrode carrier 100 and are preferably recessed in the electrode carrier 100 so that they do not make physical contact with an object placed on the electrode carrier 100. There are eighty five electrodes, each denoted in FIG. 1 by a dot, and for ease of reference indicated by reference numerals 1 to 85 respectively. The electrodes 1-85 are arranged equidistant in a triangular matrix, such that the electrodes 1-85 are located at corners of equilateral triangles arranged in a continuum. In such an arrangement, each electrode 1-85, except those adjacent the boundary of the arrangement, has six nearest neighbour electrodes 1-85 which are arranged in a hexagon. For example, the nearest neighbours to electrode 7 are electrodes 1, 2, 6, 8, 14, 15. In FIG. 1, the electrodes 1-85 are illustrated positioned on a triangular grid 110. This is purely for the purpose of illustrating the arrangement of the electrodes 1-85 and the grid is not necessarily present in the physical implementation of the electrode carrier 100. A more dense triangular matrix could alternatively be provided by subdividing each equilateral triangle into four smaller equilateral triangles by means of additional lines parallel to the grid lines depicted in FIG. 1.

The electrodes 1-85 are numbered in the following manner in eleven horizontal rows of the triangular matrix. The numbers increase from left to right of each row and increase from the bottom row to the top row. The electrodes of each row are positioned symmetrically with respect to the electrodes of the adjacent row or rows. The first to eleventh rows contain, respectively, the electrodes having the following numbers: 1-4; 5-11; 12-19; 20-28; 29-38; 39-47; 48-57; 58-66; 67-74; 75-81; 82-85.

Each electrode 1-85 is coupled to a switching device 200, although in FIG. 1 for clarity the individual couplings of each electrode 1-85 are not illustrated. The switching device 200 is coupled to a transceiver 300. The transceiver 300 generates an input signal which is routed by the switching device 200 to a selected input electrode pair of the electrodes 1-85. The transceiver 300 also receives output signals routed by the switch device 200 from a selected output electrode group of the electrodes 1-85. The input signal may be an alternating voltage applied across the selected input electrode pair, in which case the output signals may be electric currents measured at the selected output electrode group. Alternatively, the input signal may be an alternating electric current applied at the selected input electrode pair, in which case the output signals may be voltages measured at the selected output electrode group. The transceiver 300 may generate the input signal at different frequencies in the range, for example 100 Hz to 10 MHz.

The switching device 200 is coupled to a controller 400 for controlling the selection of the input electrode pair at which the input signal is applied and the selection of the output electrode group from which the output signals are to be received. The transceiver 300 is coupled to the controller 400 which co-ordinates the generation of the input signal by the transceiver 300 and the selection of the input electrode pair and the output electrode group by the switching device 200.

The switching device 200, the transceiver 300 and the controller 400 may be integral with the electrode carrier 100. This enables short couplings between the electrodes 1-85 and the switching device 200, between the switching device 200 and the transceiver 300, and between the transceiver 300 and the controller 400, which facilitates the use of a high frequency for the input signals.

The controller 400 can have a user interface for controlling the selection of the input electrode pair and the output electrode group by the switching device 200. Alternatively, the controller 400 can select a fixed input electrode pair for applying the input signal and select a fixed output electrode group for receiving the output signals. In addition, the controller 400 receives from the transceiver 300 indications of the output signals received by the transceiver 300. From the indications of the output signals, and from data characterising the input signal, the controller 400 evaluates the electrical impedance of an object under evaluation. The controller 400 is coupled to a display device 500 for displaying an image representative of the electrical impedance. In addition, the controller 400 may perform diagnosis based on the electrical impedance.

Figure 2:
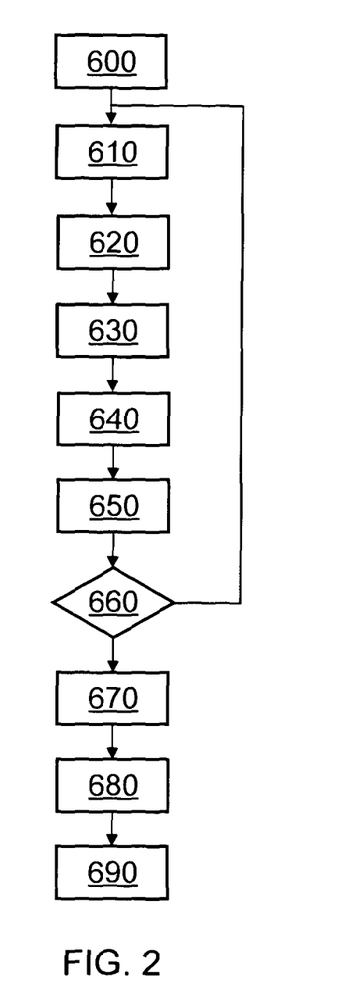
FIG. 2 is a flow chart of a method of electrical impedance detection.

Referring to FIG. 2 there is illustrated a method of electrical impedance detection. At step 600, an object to be evaluated, for example body tissue such as a human breast, is placed adjacent the electrode carrier 100, either in contact with the electrode carrier 100, or spaced apart from the electrode carrier 100 by an electrically conductive liquid 770 or spacing member 760, described below with reference to FIG. 8.

Figure 3:
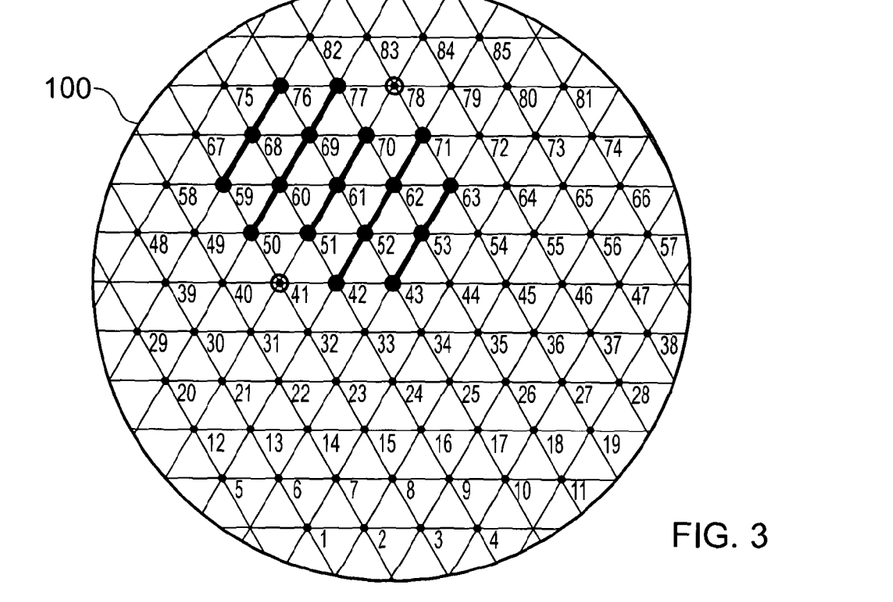
FIG. 3 is a schematic diagram of electrodes mounted on an electrode carrier illustrating electrodes in use.

At step 610, a first input electrode pair is selected by the controller 400 for the application of a first input signal. FIG. 3 shows an example of the first input electrode pair comprising electrodes 41 and 78, highlighted by circles. For convenience, the first input electrode pair will be referred to as $P_1$, where $P_1=\{41, 78\}$. The electrodes of the first input electrode pair $P_1$ are spaced apart by a distance equal to four times the length of a side of the equilateral triangles.

At step 620, a first output electrode group is selected by the controller 400 for receiving first output signals. FIG. 3 shows an example of a first output electrode group comprising electrodes 42, 43, 51-53, 59-63, 68-71, 76 and 77. For convenience the first output group of electrodes will be referred to as $G_1$, where $G_1=\{42, 43, 51-53, 59-63, 68-71, 76, 77\}$. The electrodes of the first output electrode group $G_1$, together with the electrodes of the first input electrode pair $P_1$, will be referred to as a first electrode set $S_1$. The nineteen electrodes of the first electrode set $S_1$ are arranged in a first pattern, and the boundary of the first pattern is a first hexagon comprising electrodes 41-43, 50, 53, 59, 63, 68, 71, 76-78. Each side of the first hexagon has a length equal to twice the length of a side of the equilateral triangles. The electrodes of the first input electrode pair $P_1$ are located at opposite corners of the first hexagon.

At step 630 the first input signal is applied by the transceiver 300 to the electrodes 41 and 78 of the first input electrode pair $P_1$.

At step 640 the first output signals are received by the transceiver 300 from the electrodes 42, 43, 51-53, 59-63, 68-71, 76 and 77 of the first output electrode group $G_1$. In particular, within this first output electrode group $G_1$, the first output signals are measured between the following combinations of electrodes:

42 and 52; 43 and 53;
50 and 60; 51 and 61; 52 and 62; 53 and 63;
59 and 68; 60 and 69; 61 and 70; 62 and 71;
68 and 76; 69 and 77.

In FIG. 3, these combinations of electrodes are highlighted by being joined by bold lines.

Each of these combinations comprises two adjacent electrodes. The combination 51 and 61 and the combination 61 and 70 lie on a first line coincident with a line joining the electrodes 41 and 78 of the first input electrode pair $P_1$. The combination 42 and 52, the combination 52 and 62, and the combination 62 and 71 lie on a second line parallel to the first line, and joining corners of the first hexagon adjacent to those corners of the first hexagon occupied by the electrodes 41 an 78 of the first input electrode pair $P_1$. The combination 50 and 60, the combination 60 and 69, and the combination 69 and 77 lie on a third line parallel to the first line and on the opposite side of the first line to the second line, and joining further corners of the first hexagon adjacent to those corners of the first hexagon occupied by the electrodes 41 and 78 of the first input electrode pair $P_1$. The combination 43 and 53 and the combination 53 and 63 lie on a fourth line parallel to the first line and on the same side of the first line as the second line, and joining corners of the first hexagon furthest from the electrodes 41 and 78 of the first input electrode pair $P_1$. The combination 59 and 68 and the combination 68 and 76 lie on a fifth line parallel to the first line and on the same side of the first line as the third line, and joining further corners of the first hexagon furthest from the electrodes 41 and 78 of the first input electrode pair $P_1$.

At step 650 the controller 400 receives from the transceiver 300 indications of the first output signals received by the transceiver 300. The controller 400 stores these indications.

At step 660 the controller 400 determines whether the steps 610 to 650 are required to be repeated for another input electrode pair and another output electrode group. If the steps 610 to 650 are required to be repeated, flow returns to step 610.

Figure 4:
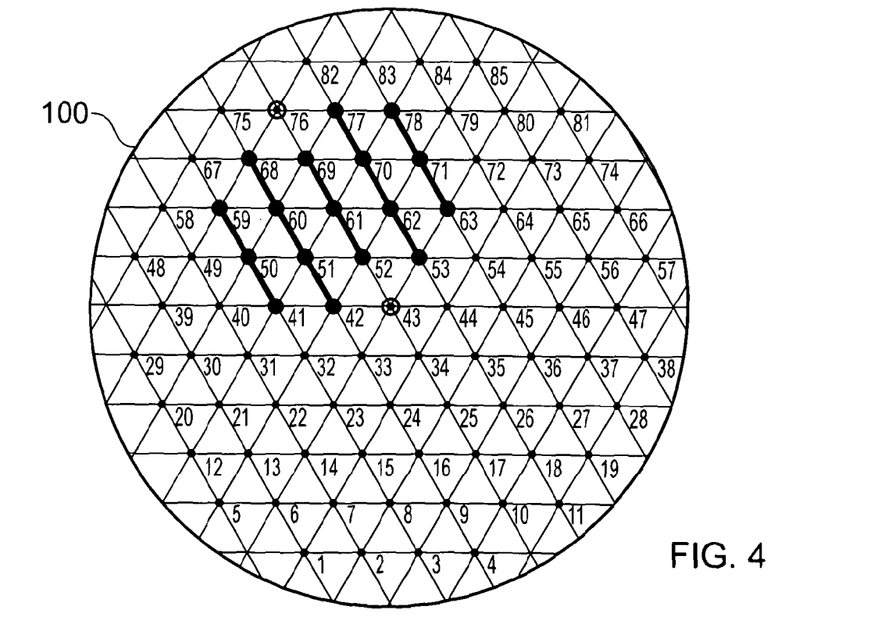
FIG. 4 is a schematic diagram of electrodes mounted on an electrode carrier illustrating other electrodes in use.

For example, if the steps 610 to 650 are required to be repeated for a second input electrode pair and a second output electrode group, at step 610 on the second pass, a second input electrode pair is selected by the controller 400 for the application of a second input signal. FIG. 4 shows an example of a second input electrode pair $P_2$ comprising electrodes 43 and 76, highlighted by circles, i.e. $P_2=\{43, 76\}$. The second input electrode pair $P_2$ comprising electrodes 43 and 76 is aligned relative to the first input electrode pair $P_1$ comprising electrodes 41 and 78 at an anticlockwise rotational displacement of 60°, or equivalently a clockwise rotational displacement of 120°. Also, the spacing of the electrodes $\{41, 78\}$ of the first input electrode pair $P_1$ is the same as the spacing of the electrodes $\{43, 76\}$ of the second input electrode pair $P_2$, namely a distance equal to four times the length of a side of the equilateral triangles. Thus the electrodes of the second input electrode pair $P_2$ occupy corners of the first hexagon adjacent to the corners occupied by the electrodes of the first input electrode pair.

At step 620 on the second pass, a second output electrode group is selected by the controller 400 for receiving second output signals. FIG. 4 shows an example of a second output electrode group $G_2$ comprising electrodes 41, 42, 50-53, 59-63, 68-71, 77 and 78, i.e. $G_2=\{41, 42, 50-53, 59-63, 68-71, 77, 78\}$. The electrodes of the second output electrode group $G_2$, together with the electrodes of the second input electrode pair $P_2$, will be referred to as a second electrode set $S_2$. The nineteen electrodes of the second electrode set $S_2$ are arranged in a second pattern, and the boundary of the second pattern comprises electrodes 41-43, 50, 53, 59, 63, 68, 71, 76-78, which is coincident with the first hexagon.

At step 630 on the second pass, a second input signal is applied by the transceiver 300 to the electrodes $\{43, 76\}$ of the second input electrode pair $P_2$.

At step 640 on the second pass, second output signals are received by the transceiver 300 from the electrodes of the second output electrode group $G_2$. In particular, within the second output electrode group $G_2$, the second output signals are measured between the following combinations of electrodes:

41 and 50; 42 and 51;
50 and 59; 51 and 60; 52 and 61; 53 and 62;
60 and 68; 61 and 69; 62 and 70; 63 and 71;
70 and 77; 71 and 78.

In FIG. 4, these combinations of electrodes are highlighted by being joined by bold lines.

Each of these combinations comprises two adjacent electrodes. The combination 52 and 61 and the combination 61 and 69 lie on a sixth line coincident with a line joining the electrodes 43 and 76 of the second input electrode pair $P_2$. The combination 42 and 51, the combination 51 and 60, and the combination 60 and 68 lie on a seventh line parallel to the sixth line, and joining corners of the first hexagon adjacent to those corners of the first hexagon occupied by the electrodes 43 and 78 of the second input electrode pair $P_2$. The combination 53 and 62, the combination 62 and 70, and the combination 70 and 77 lie on an eighth line parallel to the sixth line and on the opposite side of the sixth line to the seventh line, and joining further corners of the first hexagon adjacent to those corners of the first hexagon occupied by the electrodes 43 an 76 of the second input electrode pair $P_2$. The combination 41 and 50 and the combination 50 and 59 lie on a ninth line parallel to the sixth line and on the same side of the sixth line as the seventh line, and joining corners of the first hexagon furthest from the electrodes 43 and 76 of the second input electrode pair $P_2$. The combination 63 and 71 and the combination 71 and 78 lie on a tenth line parallel to the sixth line and on the same side of the sixth line as the eighth line, and joining further corners of the first hexagon furthest from the electrodes 43 and 76 of the second input electrode pair $P_2$.

It can be readily appreciated from FIGS. 3 and 4 that the second input electrode pair $P_2$ and the combinations of electrodes from the second output electrode group $G_2$ form an identical pattern to the first input electrode pair $P_1$ and the combinations of electrodes from the first output electrode group $G_1$, except for an anticlockwise rotation by 60°, or equivalently a clockwise rotation by 120°.

At step 650 on the second pass, the controller 400 receives from the transceiver 300 indications of the second output signals received by the transceiver 300. The controller 400 stores these indications.

At step 660 on the second pass, the controller 400 determines whether the steps 610 to 650 are required to be repeated for another input electrode pair and another output group of electrodes. If the steps 610 to 650 are required to be repeated, flow returns to step 610.

Figure 5:
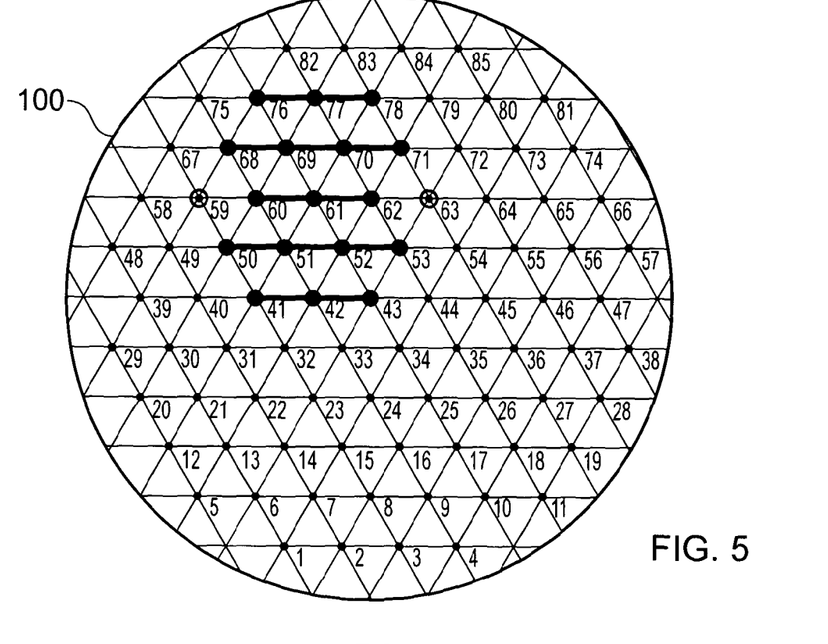
FIG. 5 is a schematic diagram of electrodes mounted on an electrode carrier illustrating further electrodes in use.

For example, if the steps 610 to 650 are required to be repeated for a third input electrode pair and a third output group of electrodes, at step 610 on the third pass, a third input electrode pair is selected by the controller 400 for the application of a third input signal. FIG. 5 shows an example of a third input electrode pair $P_3$ comprising electrodes 59 and 63, highlighted by circles, i.e. $P_3=\{59, 63\}$. The third input electrode pair $P_3$ comprising electrodes 59 and 63 is aligned relative to the first input electrode pair $P_1$ and relative to the second input electrode pair $P_2$ at a rotational displacement of 60°, or equivalently 120°. Also, the spacing of the electrodes $\{59, 63\}$ of the third input electrode pair $P_3$ is the same as the spacing of the electrodes $\{43, 76\}$ of the first input electrode pair $P_1$ and of the second input electrode pair $P_2$.

At step 620 on the third pass, a third output group of electrodes is selected by the controller 400 for receiving third output signals. FIG. 5 shows an example of a third output group of electrodes $G_3$ comprising electrodes 41-43, 50-53, 60-62, 68-71, and 76-78, i.e. $G_2=\{41-43, 50-53, 60-62, 68-71, 76-78\}$. The electrodes of the third output group of electrodes $G_3$, together with the electrodes of the third input electrode pair $P_2$, will be referred to as the third electrode set $S_3$. The nineteen electrodes of the third electrode set $S_3$ are arranged in a third pattern, and the boundary of the third pattern comprises electrodes 41-43, 50, 53, 59, 63, 68, 71, 76-78, which is coincident with the first hexagon.

At step 630 on the third pass, a third input signal is applied by the transceiver 300 to the electrodes {59, 63} of the third input electrode pair $P_3$.

At step 640 on the third pass, third output signals are received by the transceiver 300 from the electrodes of the third output group of electrodes $G_3$. In particular, within the third output group of electrodes $G_3$, the third output signals are measured between the following combinations of electrodes:

41 and 42; 42 and 43;
50 and 51; 51 and 52; 52 and 53;
60 and 61; 61 and 62;
68 and 69; 69 and 70; 70 and 71;
76 and 77; 77 and 78.

In FIG. 5, these combinations of electrodes are highlighted by being joined by bold lines.

Each of these combinations comprises two adjacent electrodes. The combination 60 and 61 and the combination 61 and 62 lie on an eleventh line coincident with a line joining the electrodes 59 and 63 of the third input electrode pair $P_3$. The combination 68 and 69, the combination 69 and 70, and the combination 70 and 71 lie on a twelfth line parallel to the eleventh line, and joining corners of the first hexagon adjacent to those corners of the first hexagon occupied by the electrodes 59 and 63 of the third input electrode pair $P_3$. The combination 50 and 51, the combination 51 and 52, and the combination 52 and 53 lie on a thirteenth line parallel to the eleventh line and on the opposite side of the eleventh line to the twelfth line, and joining further corners of the first hexagon adjacent to those corners of the first hexagon occupied by the electrodes 59 an 63 of the third input electrode pair $P_3$. The combination 76 and 77 and the combination 77 and 78 lie on a fourteenth line parallel to the eleventh line and on the same side of the eleventh line as the twelfth line, and joining corners of the first hexagon furthest from the electrodes 59 and 78 of the third input electrode pair $P_3$. The combination 41 and 42 and the combination 42 and 43 lie on a fifteenth line parallel to the eleventh line and on the same side of the eleventh line as the thirteenth line, and joining further corners of the first hexagon furthest from the electrodes 59 and 63 of the third input electrode pair $P_3$.

It can be readily appreciated from FIGS. 3 and 5 that the third input electrode pair $P_3$ and the combinations of electrodes from the third output electrode group $G_3$ form an identical pattern to the first input electrode pair $P_1$ and the combinations of electrodes from the first output electrode group $G_1$, except for a clockwise rotation by 60°, or equivalently an anticlockwise rotation by 120°.

At step 650 on the third pass, the controller 400 receives from the transceiver 300 indications of the third output signals received by the transceiver 300. The controller 400 stores these indications.

At step 660 on the third pass, the controller 400 determines whether the steps 610 to 650 are required to be repeated for another input electrode pair and another output group of electrodes. If the steps 610 to 650 are required to be repeated, flow returns to step 610.

If the steps 610 to 650 are not required to be repeated, flow continues to step 670 where the controller 400 employs the stored indications of the first, second and third output signals to evaluate the electrical impedance of the object being evaluated. For this evaluation the controller 400 may also employ data characterising the first, second and third input signals.

At step 680, the controller 400 may format for display data representative of the electrical impedance of the object being evaluated, and transmit the formatted data to the display device 500 which displays an image representative of the electrical impedance.

At step 690, the controller 400 may perform diagnosis based on the electrical impedance of the object being evaluated. For example, the diagnosis may be performed by comparing the evaluated electrical impedance with stored reference data representative of the impedance of an object in different medical conditions.

Figure 6:
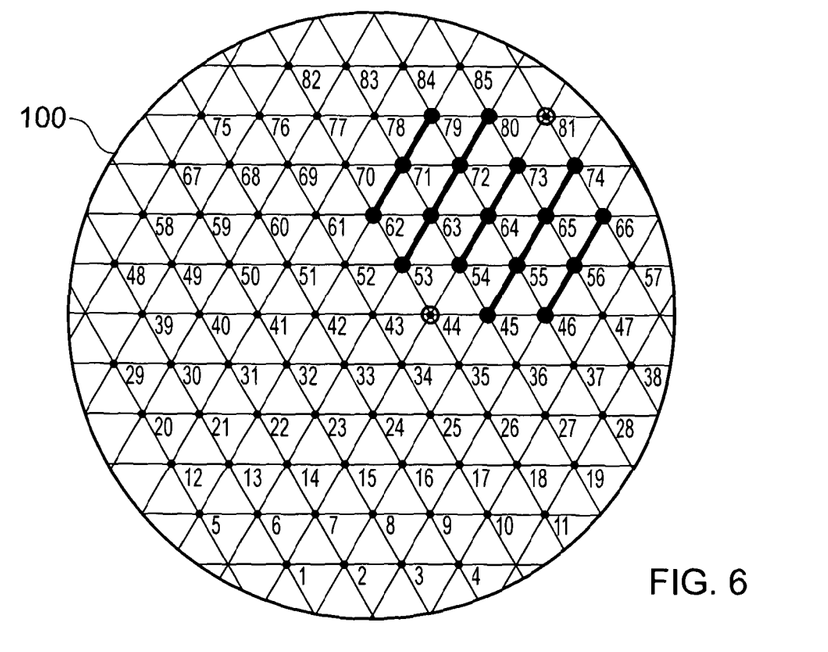
FIG. 6 is a schematic diagram of electrodes mounted on an electrode carrier illustrating yet further electrodes in use.

The method step 610 to 650 illustrated by the flow chart of FIG. 2 may also be performed in further passes for further pairs of electrodes which are displaced from the first, second and third input electrode pairs $P_1$, $P_2$, $P_3$, and for further output electrode groups which are displaced from the first, second and third output electrode groups $G_1$, $G_2$, $G_3$ by a common distance and a common direction. FIG. 6 shows an example of a fourth input electrode pair $P_4$ comprising electrodes 44 and 81, highlighted by circles, i.e. $P_4$={44, 81}, and a fourth output electrode group $G_4$ comprising electrodes 44-46, 53-56, 62-66, 71-74, 79-81, i.e. $G_4$={44-46, 53-56, 62-66, 71-74, 79-81}. The electrodes of the fourth output electrode group $G_4$, together with the electrodes of the fourth input electrode pair $P_4$, will be referred to as a fourth electrode set $S_4$. The nineteen electrodes of the fourth electrode set $S_4$ are arranged in a fourth pattern, and the boundary of the fourth pattern comprises the electrodes 44-46, 53, 56, 62, 66, 71, 74, 79-81 and form a second hexagon.

With such a displacement, at step 630 on a fourth pass, a fourth input signal is applied by the transceiver 300 to the electrodes {44, 81} of the fourth input electrode pair $P_4$, and at step 640 on the fourth pass, fourth output signals are received by the transceiver 300 from the electrodes of the fourth output group of electrodes $G_4$. In particular, within this fourth output group of electrodes $G_4$, the first output signals are measured between the following combinations of electrodes:

45 and 55; 46 and 56;
53 and 63; 54 and 64; 55 and 65; 56 and 66;
62 and 71; 63 and 72; 64 and 73; 65 and 74;
71 and 79; 72 and 80.

In FIG. 6, these combinations of electrodes are highlighted by being joined by bold lines.

Each of these combinations comprises two adjacent electrodes. The combination 54 and 64 and the combination 64 and 73 lie on an sixteenth line coincident with a line joining the electrodes 44 and 81 of the fourth input electrode pair $P_4$. The combination 53 and 63, the combination 63 and 72, and the combination 72 and 80 lie on a seventeenth line parallel to the sixteenth line, and joining corners of the second hexagon adjacent to those corners of the second hexagon occupied by the electrodes 44 and 81 of the fourth input electrode pair $P_4$. The combination 45 and 55, the combination 55 and 65, and the combination 65 and 74 lie on an eighteenth line parallel to the sixteenth line and on the opposite side of the sixteenth line to the seventeenth line, and joining further corners of the second hexagon adjacent to those corners of the second hexagon occupied by the electrodes 44 an 81 of the fourth input electrode pair $P_4$. The combination 62 and 71 and the combination 71 and 79 lie on a nineteenth line parallel to the sixteenth line and on the same side of the sixteenth line as the seventeenth line, and joining corners of the second hexagon furthest from the electrodes 44 and 81 of the fourth input electrode pair $P_4$. The combination 46 and 56 and the combination 56 and 66 lie on a twentieth line parallel to the sixteenth line and on the same side of the sixteenth line as the eighteenth line, and joining further corners of the second hexagon furthest from the electrodes 44 and 81 of the fourth input electrode pair $P_4$.

It can be readily appreciated from FIGS. 3 and 6 that the fourth input electrode pair $P_4$ and the combinations of electrodes from the fourth output electrode group $G_4$ form an identical hexagonal pattern to the first input electrode pair $P_1$ and the combinations of electrodes from the first output electrode group $G_1$, except for a displacement of each electrode of the fourth electrode set $S_4$ relative to the corresponding electrodes of the first electrode set $S_1$ by a common distance of three times the length of the side of the equilateral triangles, and by a common direction, namely horizontally to the right.

At step 650 on the third pass, the controller 400 receives from the transceiver 300 indications of the fourth output signals received by the transceiver 300. The controller 400 stores these indications for subsequent evaluation of the electrical impedance of the object being evaluated.

Further passes of steps 610 to 650 may be made, if desired, with a fifth input electrode pair $P_5$ and a fifth output electrode group $G_5$ which are a horizontal displacement to the right by three electrode positions of, respectively, the second input electrode pair $P_2$ and the second output electrode group $G_2$, and with a sixth input electrode pair $P_6$ and a sixth output electrode group $G_6$ which are a horizontal displacement to the right by three electrode positions of, respectively, the third input electrode pair $P_3$ and the third output electrode group $G_3$. The displacement of the arrangement of the input electrode pairs and of the pattern of the output electrode groups by a common distance and a common direction, that is a lateral displacement, may be used for localisation of an area of interest in an object, whereas the rotational displacement of the arrangement of the pairs of electrodes and of the pattern of the groups of electrodes may be used for increasing the resolution of the electrical impedance evaluation.

Figure 7:
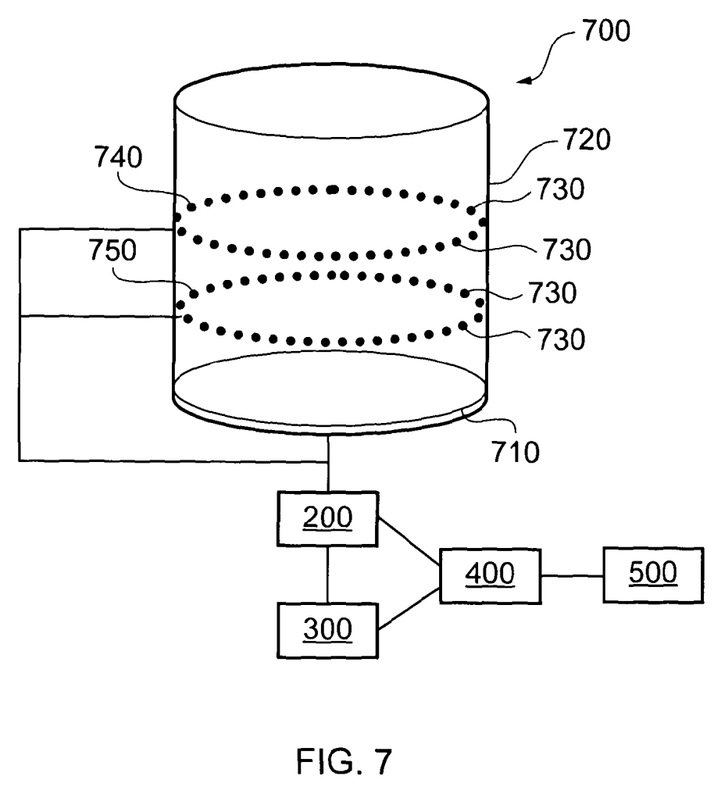
FIG. 7 is a schematic diagram of an apparatus for electrical impedance imaging comprising a receptacle having electrodes.

Referring to FIG. 7, a receptacle 700 which is cylindrical has a base 710 which is circular comprising the electrode carrier 100, with the electrodes 1-85 exposed to the interior of the receptacle 700 for electrical impedance imaging of an object within the receptacle 700. The electrodes 1-85 are not illustrated in FIG. 7 for clarity. The electrode carrier 100 may be the whole base 710, or a part of the base 710. The receptacle 700 has a wall 720. Further electrodes 730 are deployed across the wall 720 and are exposed to the interior of the receptacle 700 for electrical impedance imaging of an object within the receptacle 700. Preferably, the further electrodes 730 are recessed in the wall 720 so that they do not make physical contact with the object in the receptacle 700, but can make electrical contact with the object by means of an electrically conductive liquid in the receptacle 700. The further electrodes 730 are arranged in a first ring 740 and a second ring 750. Each ring has thirty-six of the further electrodes 730 equally spaced. Alternatively, other numbers of the further electrodes 730 may be used. The switching device 200 can be coupled to each of the further electrodes 730, although in FIG. 7 for clarity the individual couplings to each of the further electrodes 730 are not illustrated. The input signal generated by the transceiver 300 can be routed by the switching device 200, under the control of the controller 400, to a selected input electrode pair, or more than one pair in different ones of the first and second rings 740, 750, of the further electrodes 730. The transceiver 300 receives output signals routed by the switch device 200 from selected ones of the further electrodes 730 under the control of the controller 400. The controller 400 co-ordinates the generation of the input signal by the transceiver 300 and the selection of the further electrodes 730 by the switching device 200. The selection of the further electrodes 730 may be made from the first ring 740 or from the second ring or from both rings 740, 750. Furthermore, none of the further electrodes 730 may be selected if it is desired to make electrical impedance measurements using only the electrodes 1-85 of the electrode carrier 100. Also, the selection of the further electrodes 730 may be made simultaneous to, or independently of, the selection of the input electrode pair $P_1$, $P_2$, $P_3$, $P_4$, $P_5$, $P_6$ at which the input signal is applied and the selection of the output electrode group $G_1$, $G_2$, $G_3$, $G_4$, $G_5$, $G_6$ from which the output signals are to be received. The controller 400 receives from the transceiver 300 indications of the output signals received by the transceiver 300 from the selected further electrodes 730 and evaluates the electrical impedance of the object under evaluation.

In a variation of the embodiment described with reference to FIG. 7, the electrode carrier 100, which is the whole or a part of the base 710, is rotatable relative to the wall 720 of the receptacle 700. The rotation takes place in the plane of the flat surface 105. This enables electrical impedance detection using a finer resolution by enabling the position of the electrodes 1-85 to be changed relative to the position of the further electrodes 730.

Figure 8:
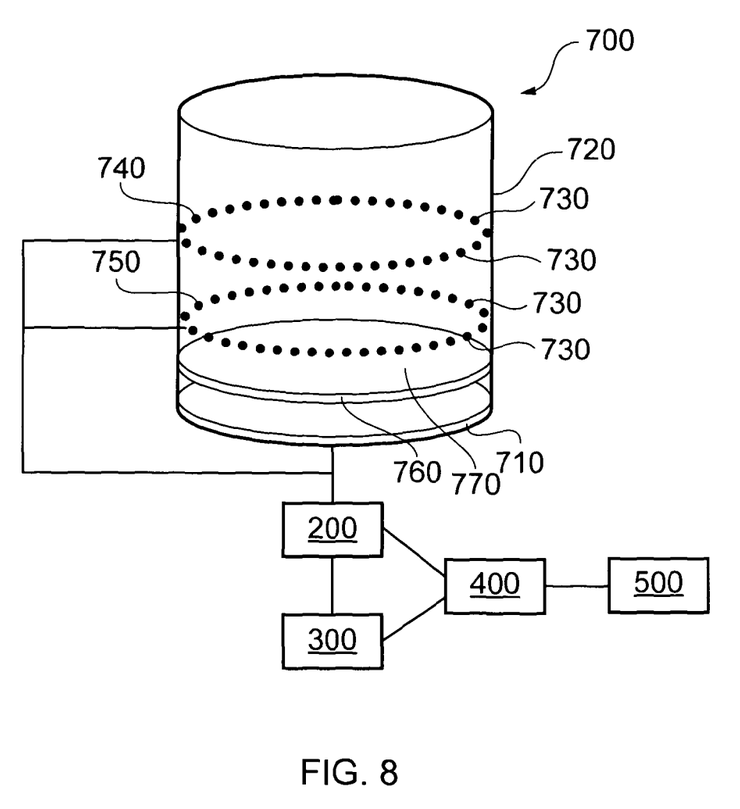
FIG. 8 is a schematic diagram of an apparatus for electrical impedance imaging comprising a spacing member.

Referring to FIG. 8, another embodiment of an apparatus for electrical impedance imaging comprises a spacing member 760 for spacing an object under evaluation from the electrode carrier 100. All other elements illustrated in FIG. 8 are identical to the elements illustrated in FIG. 7 and have corresponding reference numerals, and will not be described again. The spacing member 760 is located within the receptacle 700 and in use an object to be evaluated is placed against the spacing member 760 on the opposite side of the spacing member 760 to the electrode carrier 100. The spacing member 760 may be in contact with the base 710, or spaced from the base 710. When the electrode carrier 100 rotates relative to the wall 720, the spacing member 760 and the object do not rotate relative to the wall 720. In this way, the object is shielded from rotational forces from the rotating carrier 100, and discomfort to a patient can be reduced or eliminated.

The spacing member 760 may be electrically conductive. Typically, the spacing member 760 has a conductivity less than the conductivity of the object under evaluation.

In use, the receptacle 700 may contain an electrically conductive liquid 770. The liquid 770 may occupy the volume, if any, between the base 710 and the spacing member 760, and may also be present on the opposite side of the spacing member 760 to the base 710, where the object is placed for evaluation. The conductivity of the spacing member 760 and of the liquid 770 is typically substantially the same. Preferably, the conductivity of the spacing member 760 is at least 90% of the conductivity of the liquid 770. A preferred conductivity of the liquid 770 will depend on the conductivity of the object to be evaluated by electrical impedance imaging, but a conductivity of the liquid 770 in the range 10 to 12 mS/cm is suited to typical objects, such as human breast tissue. Such a liquid may be, for example, a saline solution having a concentration of 0.9% at 20° C.

Although embodiments have been described which have eighty five electrodes mounted on the electrode carrier 100, a greater or smaller number of electrodes may be used. In a non-illustrated variant of the electrode carrier 100, some of the electrodes 1-85 may be omitted, in which case the electrodes 1-85 are not equidistant. In such an arrangement, the electrodes 1-85 are nevertheless located at corners of equilateral triangles arranged in a continuum, although not at all available corners of the equilateral triangles. This variant may be used when the union of the different input electrode pairs and output electrode groups $\{P_1, P_2, P_3, P_4, P_5, P_6, G_1, G_2, G_3,$ $G_4, G_5, G_6\}$ for all selectable input electrode pairs and output electrode groups does not encompass all available corners of the equilateral triangles. This variant enables the number of connections to the electrodes 1-85 to be reduced.

Preferably, one or more of the electrodes 1-85 and further electrodes 730 have a surface that has been polished to make it smooth. A smooth surface can enhance the repeatability of the measurements of the output signals.

Although embodiments have been described in which the electrode carrier 100 is circular, this is not essential and an electrode carrier having a different shape can be used. Although embodiments have been described in which the electrodes 1-85 are deployed across a flat surface 105 of the electrode carrier 100, it is not essential for the surface to be flat. For example, the surface may be curved, or contoured to match the shape of an object to be evaluated. Although embodiments have been described in which rotation of the electrode carrier 100 takes place in the plane of the flat surface 105 of the electrode carrier 100, if the surface of the electrode carrier 100 is not flat, rotation may take place about an axis that is perpendicular to the surface of the electrode carrier 100 and that preferably passes through the centre of the electrode carrier 100.

Although embodiments have been described which employ up to five input electrode pairs $P_1, P_2, P_3, P_4, P_5, P_6$ and five output electrode groups $G_1, G_2, G_3, G_4, G_5, G_6$, other numbers may be employed. The number of different input electrode pairs $P_1, P_2, P_3, P_4, P_5, P_6$ and output electrode groups $G_1, G_2, G_3, G_4, G_5, G_6$ may be selectable by a user or by the controller 400, or may be fixed. By using more input electrode pairs $P_1, P_2, P_3, P_4, P_5, P_6$ and output electrode groups $G_1, G_2, G_3, G_4, G_5, G_6$, more data can be generated from the output signals, enabling the electrical impedance of the object to be determined with greater resolution.

The rotational displacement of the different input electrode pairs $P_1, P_2, P_3, P_4, P_5, P_6$ may be selected by a user or by the controller 400, or may be fixed. In general, this rotational displacement is a multiple of 60°, that is 60°, 120 or 180°. Correspondingly, the rotational displacement of the different output electrode groups $G_1, G_2, G_3, G_4, G_5, G_6$ may be selectable by the user or by the controller 400, or may be fixed. This rotational displacement is also a multiple of 60°, that is 60°, 120° or 180°.

Although embodiments have been described which employ a single spacing of the electrodes of the input electrode pairs $P_1, P_2, P_3, P_4, P_5, P_6$, more than one spacing may be employed. The spacing or spacings may be selectable by a user or by the controller 400, or may be fixed.

Although embodiments have been described in which each output electrode group $G_1, G_2, G_3, G_4, G_5, G_6$ employs seventeen electrodes, more or fewer electrodes may be employed. The number of electrodes in the different output electrode groups $G_1, G_2, G_3, G_4, G_5, G_6$ may be selectable by a user or by the controller 400, or may be fixed.

Although embodiments have been described which employ a hexagonal pattern of electrodes, other patterns may be used.

Although embodiments have been described which employ a hexagonal pattern of electrodes in which the sides of the hexagon have a length equal to twice the length of the side of the equilateral triangles, other multiples of the length of the side of the equilateral triangles may be used.

Although embodiments have been described which employ a single pattern for the output electrode groups $G_1, G_2, G_3, G_4, G_5, G_6$, the pattern may be selectable by the user or by the controller 400. The selection may be made from a plurality of fixed patterns, or may be made by selecting a plurality of individual electrodes. The patterns may be of different shapes, or may have the same shape and be of different sizes.

Although embodiments have been described in which the electrodes of an electrode set comprise all electrodes of the electrode carrier within a boundary, and in particular a hexagonal bounday, it is not essential that the set comprises all of the electrodes within the boundary. In other words, one or more of the electrodes within the boundary may be excluded from the electrode set, and therefore remain unused for the electrode set. For example, in the case of a hexagonal pattern of electrodes having a hexagonal boundary, one or more electrodes in a central region of the hexagon may remain unused. Although embodiments have been described in which the first and second output electrical signals are detected at a plurality of combinations of electrodes of the first and second output electrode group respectively, each of the combinations comprising adjacent electrodes, it is not essential for the electrodes of each combination to be adjacent. Furthermore, the spacing of the electrodes of the combinations of electrodes may be selectable. The electrodes of each combination, and their spacing, may be selected by the controller 400.

Although embodiments have been described in which lateral displacement of a pattern of electrodes is performed horizontally, other directions of lateral displacement may be used.

Preferably, the first, second and third input signals are identical.

Although the embodiments of FIGS. 7 and 8 comprise a receptacle 700 which is cylindrical, the receptacle 700 need not be cylindrical. Similarly, the base 710 need not be circular. The further electrodes 730 may be arranged in any number of rings, and indeed need not be arranged in rings 740, 750 but may instead be arranged in other configurations. The electrode carrier 100 may be moveable relative to the wall 720 in order to varying the volume of the receptacle 700, for example to adjust the volume to objects of different sizes under evaluation.

Although embodiments have been described in which the electrodes are arranged at corners of triangles, this is not essential and other arrangements of electrodes may be used, for example the electrodes may be arranged on five or more lines passing through a common point.

From reading the present disclosure, other variations and modifications will be apparent to the skilled person. Such variations and modifications may involve equivalent and other features which are already known in the art of electrical impedance imaging for medical diagnostics, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub combination.

It should be noted that the term "comprising" does not exclude other elements or steps, the term "a" or "an" does not exclude a plurality, a single feature may fulfil the functions of several features recited in the claims and reference signs in the claims shall not be construed as limiting the scope of the claims. It should also be noted that the Figures are not necessarily to scale; emphasis instead generally being placed upon illustrating the principles of the present invention.

The invention claimed is:

1. An apparatus for electrical impedance imaging, the apparatus comprising:
   electrodes arranged on an electrode carrier in an arrangement comprising a unit of repetition that repeats over the electrode carrier and that has an angle of rotational symmetry less than 90°;
   means for applying a first input electrical signal at a first input electrode pair of the electrodes;
   means for detecting first output electrical signals at a first output electrode group of the electrodes;
   means for applying a second input electrical signal at a second input electrode pair of the electrodes; and
   means for detecting second output electrical signals at a second output electrode group of the electrodes;
   wherein the second input electrode pair is aligned relative to the first input electrode pair at an angle of rotational displacement equal to one of the angles of rotational symmetry or a multiple of (one of) the angles of rotational symmetry.

2. An apparatus as claimed in claim 1, wherein the unit of repetition overlaps from one repetition to another.

3. An apparatus as claimed in claim 1, wherein the arrangement comprises one or more different units of repetition that each repeat over the electrode carrier and have angles of rotational symmetry less than 90°.

4. An apparatus as claimed in claim 1, wherein the electrodes are arranged at one or more corners of each triangle of a tessellation of triangles.

5. An apparatus as claimed in claim 4, wherein the triangles are equilateral triangles and wherein the triangles are of equal size.

6. An apparatus as claimed in claim 1, comprising means for selecting a spacing of the electrodes of the first input electrode pair and a spacing of the electrodes of the second input electrode pair.

7. An apparatus as claimed in claim 1, wherein the electrodes of the first input electrode pair and of the first output electrode group constitute a first electrode set having a first pattern, and the electrodes of the second input electrode pair and of the second output electrode group constitute a second electrode set having a second pattern, and wherein the second pattern is identical to the first pattern rotated by the angle of rotational displacement.

8. An apparatus as claimed in claim 7, comprising means for selecting a number of electrodes in the first and second electrode sets and means for selecting the first pattern.

9. An apparatus as claimed in claim 8, wherein a boundary of the first pattern is a hexagon, the hexagon having sides of length corresponding to a multiple of the length of a side of the equilateral triangles.

10. An apparatus as claimed in claim 9, wherein the first input electrode pair comprises electrodes at opposite corners of the hexagon and the first output electrode group comprises all other electrodes of the first electrode set.

11. An apparatus as claimed in claim 1, wherein the means for detecting the first output electrical signals is operable to detect the first output electrical signals at a plurality of combinations of electrodes of the first output electrode group, and the means for detecting the second output electrical signals is operable to detect the second output electrical signals at a plurality of combinations of electrodes of the second output electrode group.

12. An apparatus as claimed in claim 11, comprising means for selecting a spacing of the electrodes of each of the combinations of electrodes.

13. An apparatus as claimed in claim 12, wherein the plurality of combinations of electrodes of the first output electrode group are parallel to a line joining the electrodes of the first input electrode pair, and the plurality of combinations of electrodes of the second output electrode group are parallel to a line joining the electrodes of the second input electrode pair.

14. An apparatus as claimed in claim 13, comprising means for applying a third input electrical signal at a third input electrode pair of the electrodes and means for detecting third output electrical signals at a third output electrode group of the electrodes, wherein the third input electrode pair is displaced from the first input electrode pair and the third output electrode group is displaced from the first output electrode group by a common distance and a common direction.

15. An apparatus as claimed in claim 1, wherein the electrode carrier is at least part of a base of a receptacle for electrical impedance imaging of an object located within the receptacle, and wherein the receptacle comprises further electrodes arranged on a wall of the receptacle for electrical impedance imaging of an object located within the receptacle.

16. An apparatus as claimed in claim 15, wherein the electrode carrier is rotatable relative to the wall.

17. An apparatus as claimed in claim 16, comprising a spacing member for, spacing the object from the electrode carrier.

18. An apparatus as claimed in claim 17, wherein the spacing member is electrically conductive and the spacing member has a conductivity less than or equal to the conductivity of the object.

19. A method of electrical impedance detection, comprising:
   employing an electrode carrier having electrodes arranged on the electrode carrier in an arrangement comprising a unit of repetition that repeats over the electrode carrier and that has an angle of rotational symmetry less than 90°;
   applying a first input electrical signal at a first input electrode pair of the electrodes;
   detecting first output electrical signals at a first output electrode group of the electrodes;
   applying a second input electrical signal at a second input electrode pair of the electrodes; and
   detecting second output electrical signals at a second output electrode group of the electrodes;
   wherein the second input electrode pair is aligned relative to the first input electrode pair at an angle of rotational displacement equal to one of the angles of rotational symmetry or a multiple of (one of) the angles of rotational symmetry.

20. An apparatus for electrical impedance imaging, the apparatus comprising:
   electrodes arranged on an electrode carrier in an arrangement comprising a unit of repetition that repeats over the electrode carrier and that has an angle of rotational symmetry less than 90°; and
   a controller configured to:
      apply a first input electrical signal at a first input electrode pair of the electrodes;
      detect first output electrical signals at a first output electrode group of the electrodes;

apply a second input electrical signal at a second input electrode pair of the electrodes; and detect second output electrical signals at a second output electrode group of the electrodes;

wherein the second input electrode pair is aligned relative to the first input electrode pair at an angle of rotational displacement equal to one of the angles of rotational symmetry or a multiple of (one of) the angles of rotational symmetry.

* * * * *